US012564336B2

(12) United States Patent
Katz et al.

(10) Patent No.: US 12,564,336 B2
(45) Date of Patent: *Mar. 3, 2026

(54) REMOTE CONTROLLED PHYSICAL ACTIVITY MONITORING

(71) Applicant: 6Degrees Ltd., Tel Aviv (IL)

(72) Inventors: Aryeh Haim Katz, Safed (IL); Miri Berger Katz, Ramat-Gan (IL)

(73) Assignee: 6DEGREES LTD., Tel Aviv (IL)

( * ) Notice: Subject to any disclaimer, the term of this patent is extended or adjusted under 35 U.S.C. 154(b) by 0 days.

This patent is subject to a terminal disclaimer.

(21) Appl. No.: 18/778,367

(22) Filed: Jul. 19, 2024

(65) Prior Publication Data

US 2025/0185944 A1     Jun. 12, 2025

Related U.S. Application Data

(63) Continuation of application No. 18/090,274, filed on Dec. 28, 2022, now Pat. No. 12,070,305, which is a
(Continued)

(51) Int. Cl.
*A61B 5/11*          (2006.01)
*A61B 5/00*          (2006.01)
(Continued)

(52) U.S. Cl.
CPC .......... *A61B 5/1118* (2013.01); *A61B 5/0004* (2013.01); *A61B 5/0022* (2013.01);
(Continued)

(58) Field of Classification Search
CPC ... A61B 5/6828; A61B 5/1107; A61B 5/1122; A61B 5/6824; A61B 5/7285;
(Continued)

(56) References Cited

U.S. PATENT DOCUMENTS 6,413,190 B1     7/2002   Wood et al.
6,965,842 B2    11/2005   Rekimoto
(Continued)

FOREIGN PATENT DOCUMENTS

WO     WO-2014068371 A1     5/2014

OTHER PUBLICATIONS

International Search Report issued Jul. 7, 2015 in PCT/IB2015/051286 (2 pages).
(Continued)

*Primary Examiner* — Christopher E Leiby
(74) *Attorney, Agent, or Firm* — Goodwin Procter LLP

(57)          ABSTRACT

An apparatus for remote controlled physical activity monitoring, the apparatus comprising: at least one orientation measurer, wearable on at least one body part of a user, configured to measure orientation of a body part wearing the orientation measurer during a physical activity of the user, at least one pressure meter, wearable on at least one body part of the user, configured to measure pressure applied by muscle of a body part wearing the pressure meter during the physical activity of the user, a computer processor, associated with the orientation measurer and pressure meter, configured to derive monitoring control data from the measured orientation and pressure, and a data transmitter, associated with the computer processor, configured to transmit the monitoring control data to a physical activity monitoring device, and thereby to remotely control a monitoring of the physical activity of the user by the physical activity monitoring device.

20 Claims, 8 Drawing Sheets

Related U.S. Application Data continuation of application No. 15/551,898, filed as application No. PCT/IB2015/051286 on Feb. 19, 2015, now Pat. No. 11,571,143.

(51) Int. Cl.

| | |
|---|---|
| *A63B 24/00* | (2006.01) |
| *G06F 3/01* | (2006.01) |
| *G16H 20/30* | (2018.01) |
| *G16H 40/67* | (2018.01) |
| *G16H 10/60* | (2018.01) |

(52) U.S. Cl.

CPC .......... *A61B 5/0077* (2013.01); *A61B 5/1107* (2013.01); *A61B 5/1112* (2013.01); *A61B 5/1114* (2013.01); *A61B 5/1122* (2013.01); *A61B 5/1128* (2013.01); *A61B 5/6824* (2013.01); *A61B 5/6828* (2013.01); *A61B 5/6887* (2013.01); *A61B 5/7278* (2013.01); *A61B 5/7285* (2013.01); *A63B 24/0006* (2013.01); *A63B 24/0062* (2013.01); *G06F 3/011* (2013.01); *G06F 3/015* (2013.01); *G06F 3/017* (2013.01); *G16H 20/30* (2018.01); *G16H 40/67* (2018.01); *A61B 2503/10* (2013.01); *A61B 2562/0247* (2013.01); *A63B 2208/03* (2013.01); *A63B 2220/12* (2013.01); *A63B 2220/56* (2013.01); *A63B 2220/62* (2013.01); *A63B 2220/806* (2013.01); *A63B 2220/808* (2013.01); *A63B 2220/836* (2013.01); *A63B 2225/20* (2013.01); *A63B 2225/50* (2013.01); *G16H 10/60* (2018.01)

(58) Field of Classification Search

CPC ... A61B 5/7278; A61B 5/6887; A61B 5/1128; A61B 5/1118; A61B 5/1114; A61B 5/1112; A61B 5/0077; A61B 5/0004; A61B 5/0022; A61B 2562/0247; A61B 2503/10; G16H 40/67; G16H 20/30; G16H 10/60; G06F 3/017; G06F 3/011; G06F 3/015; G06F 19/3418; G06F 1/163; A63B 24/0062; A63B 24/0006; A63B 2220/836; A63B 2220/806; A63B 2220/62; A63B 2220/56; A63B 2220/12; A63B 2220/808; A63B 2208/03; A63B 2225/50; A63B 2225/20

See application file for complete search history.

(56) References Cited

U.S. PATENT DOCUMENTS

| | | | |
|---|---|---|---|
| 7,602,301 | B1 | 10/2009 | Stirling et al. |
| 7,970,586 | B1 | 6/2011 | Kahn et al. |
| 8,172,722 | B2 | 5/2012 | Molyneux et al. |
| 8,593,286 | B2 | 11/2013 | Razoumov et al. |
| 8,818,478 | B2 | 8/2014 | Scheffler et al. |
| 2005/0250994 | A1 | 11/2005 | Krullaards |
| 2006/0015287 | A1 | 1/2006 | Vock et al. |
| 2006/0036141 | A1 | 2/2006 | Kamath et al. |
| 2006/0079801 | A1 | 4/2006 | DeLuca et al. |
| 2008/0122931 | A1 | 5/2008 | Simbirski et al. |
| 2009/0326406 | A1 | 12/2009 | Tan et al. |
| 2009/0327171 | A1 | 12/2009 | Tan et al. |
| 2010/0022354 | A1 | 1/2010 | Fisher |
| 2011/0132181 | A1 | 6/2011 | Kockovic |
| 2011/0264238 | A1 | 10/2011 | van der Merwe et al. |
| 2012/0046901 | A1 | 2/2012 | Green et al. |
| 2012/0139731 | A1 | 6/2012 | Razoumov et al. |
| 2012/0188083 | A1 | 7/2012 | Miller, II |
| 2012/0229634 | A1 | 9/2012 | Laett et al. |
| 2013/0162852 | A1 | 6/2013 | Boyle et al. |
| 2013/0171599 | A1 | 7/2013 | Bleich et al. |
| 2013/0197681 | A1 | 8/2013 | Alberth, Jr. et al. |
| 2013/0235222 | A1 | 9/2013 | Karn et al. |
| 2013/0242105 | A1 | 9/2013 | Boyle et al. |
| 2013/0271602 | A1 | 10/2013 | Bentley et al. |
| 2014/0070957 | A1 | 3/2014 | Longinotti-Buitoni et al. |
| 2014/0135612 | A1 | 5/2014 | Yuen et al. |
| 2015/0046886 | A1 | 2/2015 | Goel et al. |
| 2015/0196802 | A1 | 7/2015 | Siegel |
| 2016/0187977 | A1 | 6/2016 | Cruz-Hernandez et al. |
| 2016/0220808 | A1 | 8/2016 | Hyde et al. |
| 2016/0256082 | A1 | 9/2016 | Ely et al. |
| 2016/0338621 | A1 | 11/2016 | Kanchan et al. |
| 2017/0082433 | A1 | 3/2017 | Huo et al. |
| 2017/0164876 | A1 | 6/2017 | Hyde et al. |
| 2017/0273746 | A1 | 9/2017 | Flexman et al. |
| 2017/0280397 | A1 | 9/2017 | Da Costa et al. |

OTHER PUBLICATIONS

Notice of Deficiencies for EP Application No. 15882489.6 dated Dec. 2, 2020, EPO, Munich, Germany.

The EP Search Report for EP Application No. 15882489.6 dated Sep. 13, 2018, EPO, Munich, Germany.

Written Opinion issued Jul. 7, 2015 in PCT/IB2015/051286 (6 pages).

REMOTE CONTROLLED PHYSICAL ACTIVITY MONITORING

CROSS-REFERENCE TO RELATED APPLICATIONS

This Application is a Continuation of U.S. patent application Ser. No. 18/090,274 filed on Dec. 28, 2022, which is a Continuation of U.S. patent application Ser. No. 15/551, 898 filed on Aug. 17, 2017, which is a U.S. National Stage entry, filed under 35 U.S.C. § 371, of International Application No. PCT/IB2015/051286, filed on Feb. 19, 2015. The entire contents of these applications are incorporated herein by reference in their entirety.

FIELD AND BACKGROUND OF THE INVENTION

The present invention relates to physical activity monitoring and, more particularly, but not exclusively to remote controlled physical activity monitoring.

Many systems are available for measuring features of a physical activity such as athletic performance by a professional athlete, or rather by an amateur one.

For example, many gyms and fitness centers are equipped with specialized systems that help track athlete's use of certain machines. The usage data may be automatically generated and downloaded to a central computer system and made available for the athlete's review. One disadvantage of such systems is that their use is confined to use with specialized machines within the walls of the gym or fitness center and very often requires the help of an operator other than the athlete.

Systems like the NIKE+™ athletic performance monitoring system (from NIKE, Inc.) allow an individual athlete to measure and collect data relating to walking or running, without confining the measurement and collection to any specific geographic location—i.e. at any desired location, be the location indoors and or outdoors.

However, not all personal exercise and athletic activities, are limited to walking and running.

For example, personal exercise may include other forms of sport—such as Biking, Swimming, Skiing, and even more extreme sports activities—such as Sky Diving, Ice Climbing, White Water Rafting, Mountaineering, etc.

Currently, in many of those forms of physical activity there is no easy or convenient system for efficiently collecting, compiling, and storing data that accurately and empirically depicts an individual's efforts when exercising.

SUMMARY OF THE INVENTION

According to one aspect of the present invention, there is provided an apparatus for remote controlled physical activity monitoring, the apparatus comprising: at least one orientation measurer, wearable on at least one body part of a user, configured to measure orientation of a body part wearing the orientation measurer during a physical activity of the user, at least one pressure meter, wearable on at least one body part of the user, configured to measure pressure applied by muscle of a body part wearing the pressure meter during the physical activity of the user, a computer processor, associated with the orientation measurer and pressure meter, configured to derive monitoring control data from the measured orientation and pressure, and a data transmitter, associated with the computer processor, configured to transmit the monitoring control data to a physical activity monitoring device, and thereby to remotely control a monitoring of the physical activity of the user by the physical activity monitoring device.

According to a second aspect of the present, there is provided an apparatus for remote controlled physical activity monitoring, the apparatus comprising: at least one orientation measurer, wearable on at one body part of a user, configured to measure orientation of a body part wearing the orientation measurer during a physical activity of the user, a computer processor, associated with the orientation measurer, configured to derive monitoring control data from the measured orientation, and a data transmitter, associated with the computer processor, configured to transmit the monitoring control data to a physical activity monitoring device, and thereby, to remotely control a monitoring of the physical activity of the user by the physical activity monitoring device.

According to a third aspect of the present, there is provided an apparatus for remote controlled physical activity monitoring, the apparatus comprising: at least one pressure meter, wearable on at least one body part of a user, configured to measure pressure applied by muscle of a body part wearing the pressure meter during a physical activity of the user, a computer processor, associated with the pressure meter, configured to derive monitoring control data from the measured pressure, and a data transmitter, associated with the computer processor, configured to transmit the monitoring control data to a physical activity monitoring device, and thereby, to remotely control a monitoring of the physical activity of the user by the physical activity monitoring device.

According to a fourth aspect of the present, there is provided a method for remote controlled physical activity monitoring, the method comprising: measuring orientation of a body part of a user during a physical activity of the user; measuring pressure applied by muscle of a body part of the user during the physical activity of the user; deriving monitoring control data from the measured orientation and pressure; and transmitting the derived monitoring control data to a physical activity monitoring device, and thereby remote controlling a monitoring of the physical activity of the user by the physical activity monitoring device.

According to a fifth aspect of the present, there is provided a method for remote controlled physical activity monitoring, the method comprising: measuring orientation of a body part of a user during a physical activity of the user, deriving monitoring control data from the measured orientation, and transmitting the derived monitoring control data to a physical activity monitoring device, and thereby remote controlling a monitoring of the physical activity of the user by the physical activity monitoring device.

According to a sixth aspect of the present, there is provided a method for remote controlled physical activity monitoring, the method comprising: measuring pressure applied by muscle of a body part of a user during a physical activity of the user, deriving monitoring control data from the measured pressure, and transmitting the derived monitoring control data to a physical activity monitoring device, and thereby remote controlling a monitoring of the physical activity of the user by the physical activity monitoring device.

Unless otherwise defined, all technical and scientific terms used herein have the same meaning as commonly understood by one of ordinary skill in the art to which this invention belongs. The materials, methods, and examples provided herein are illustrative only and not intended to be limiting.

Implementation of the method and system of the present invention involves performing or completing certain selected tasks or steps manually, automatically, or a combination thereof. Moreover, according to actual instrumentation and equipment of preferred embodiments of the method and system of the present invention, several selected steps could be implemented by hardware or by software on any operating system of any firmware or a combination thereof. For example, as hardware, selected steps of the invention could be implemented as a chip or a circuit. As software, selected steps of the invention could be implemented as a plurality of software instructions being executed by a computer using any suitable operating system. In any case, selected steps of the method and system of the invention could be described as being performed by a data processor, such as a computing platform for executing a plurality of instructions.

BRIEF DESCRIPTION OF THE DRAWINGS

The invention is herein described, by way of example only, with reference to the accompanying drawings. With specific reference now made to the drawings in detail, it is stressed that the particulars shown are by way of example and for purposes of illustrative discussion of the preferred embodiments of the present invention only, and are presented in order to provide what is believed to be the most useful and readily understood description of the principles and conceptual aspects of the invention. The description taken with the drawings making apparent to those skilled in the art how the several forms of the invention may be embodied in practice.

In the drawings.

DESCRIPTION OF THE PREFERRED EMBODIMENTS

Figure 1A:
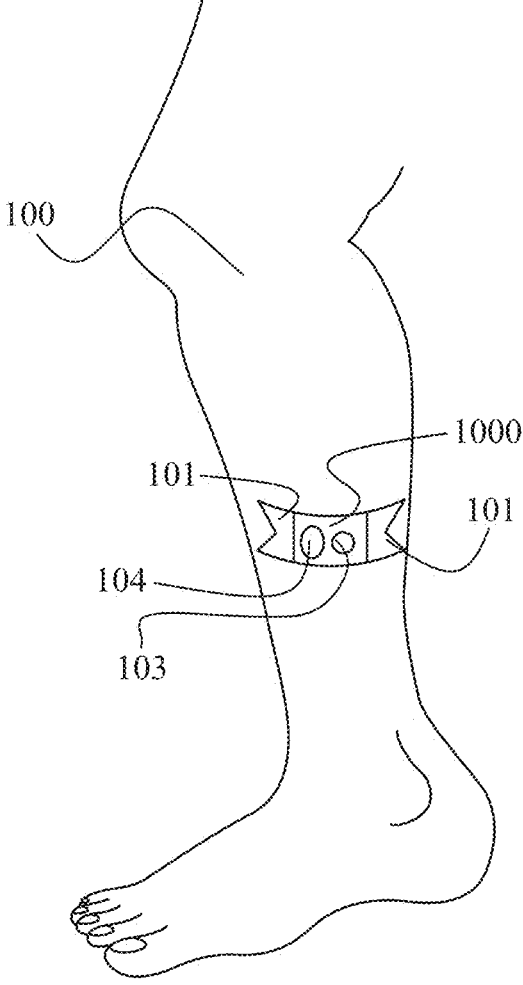
FIG. 1A is a block diagram schematically illustrating a first apparatus for remote controlled physical activity monitoring, according to an exemplary embodiment of the present invention.

The present embodiments comprise apparatuses and methods for remote controlled physical activity monitoring.

Currently, in many forms of physical activity there is no easy or convenient way for efficiently collecting, compiling and storing data that accurately and empirically depicts an individual's efforts in real time or in near real time, when exercising, as described in further detail hereinabove.

In particular, that is very often the case, when it comes to certain forms of sports—such as Biking, Swimming, Skiing, and more extreme physical forms of sport—such as Sky Diving, Ice Climbing, White Water Rafting, Mountaineering, etc.

In many of those forms of sport, when exercising, an individual usually cannot operate cameras, stoppers, or other devices, since the individual's hands are busy (say busy holding to an axe during ice climbing, or rowing during rafting).

Consequently, the individual has no way to accurately and empirically collect, compile and store data which depicts the individual's efforts during exercise.

For example, with his hands busy during the physical activity, the individual cannot operate a camera, for taking a picture of the individual exactly when the individual reaches a certain point during ice climbing, or stop a stopwatch, so as to capture the exact time in which the individual reaches an end of a swimming pool.

Thus, it is very difficult for an individual to monitor the individual's own movements while engaging in the physical activity, without the help of any other individual.

According to one exemplary embodiment of the present invention, there is provided an apparatus for remote controlled physical activity monitoring. The apparatus may include one or more orientation measurers, say Gyroscopic Devices, GPS (Global Positioning System) Receivers, etc., as described in further detail hereinbelow.

Each one of the orientation measurers is wearable on at least one body part of a user, say one on one of the user's feet and one on one of the user's arms, two on a same or different foot, one or more orientation measurers installed on a hat worn by the user, etc., as described in further detail hereinbelow.

Each one of the orientation measurers measures orientation of a body part wearing the orientation measurer during a physical activity of the user, such as Swimming, Sky Diving, Ice Climbing, Rafting, etc.

The apparatus may additionally or alternatively, include one or more pressure meters, say one or more FSR (Force Sensing Resistor) sensors, a capacitive-based pressure sensor, etc., or any combination thereof, as described in further detail hereinbelow.

Each one of the pressure meters is wearable on at least one body part of a user, say one on one of the user's feet and one on each one of the user's arms, two on a same or different foot, etc.

Each one of the pressure meters measures pressure applied by muscle of the user's body part wearing the pressure meter during the physical activity of the user, as described in further detail hereinbelow.

The apparatus further includes a computer processor in communication with the pressure meters and/or orientation measurers.

The computer processor derives monitoring control data from the measured orientation and/or pressure, as described in further detail hereinbelow.

The apparatus further includes a data transmitter, which transmits the monitoring control data to a physical activity monitoring device, and thereby remotely controls the monitoring of the physical activity of the user by the physical activity monitoring device.

Thus, in a first example, during swimming, in a pool, the user wishes a physical activity monitoring device installed on a wall opposite the pool—say a device with a video camera and a controller—to capture a certain movement that the user is about to make, in real time.

In the example, in order to instruct the camera to capture the movement, the user only has to gently shake his head in a direction predefined by a programmer or operator of the apparatus.

Specifically, in the example, the user's head movement is measured by an orientation measurer installed on a swimming hat worn by the user.

Based on the measured head movement, the computer processor, also installed on the swimming hat, derives monitoring control data which includes an instruction for the video camera to zoom in on the user.

Then, the apparatus's data transmitter transmits the derived monitoring control data to the physical activity monitoring device's controller. The controller receives the monitoring control data, and based on the received monitoring control data, immediately actuates a zooming in and image capturing operation of the camera. Consequently, the camera zooms in on the user and captures the user's image exactly when the user makes that movement.

Optionally the apparatus further includes a dedicated database on which the apparatus stores the image captured by the camera, say with metadata which indicates the time in which the image is captured, as known in the art.

In a second example, a user rafting in a canoe, and wearing a suit in which an apparatus with the above described pressure meters, orientation measurers, computer processor and data transmitter, is embedded, is allowed to control a physical activity monitoring device which includes a video camera carried by a quadcopter.

In the second example, pressure applied by muscle of the user's arm and measured by the pressure meters, and/or changes in orientation of one of the user's legs measured by the orientation measurers, are used by the user to trigger image capturing by the video camera on board the quadcopter.

Further in the second example, GPS data generated by one of the orientation measurers is used to control the quadcopter, so as to have the quadcopter follow the rafting canoe down a river, from above, as described in further detail hereinbelow.

Thus, with the present embodiment, an individual may potentially, be able to independently trigger and control an accurate empirical collection, compilation and storage of data which depicts the individual's efforts during exercise, in real time (or in near real time), without the help of another person.

The principles and operation of an apparatus and method according to the present invention may be better understood with reference to the drawings and accompanying description.

Before explaining at least one embodiment of the invention in detail, it is to be understood that the invention is not limited in its application to the details of construction and the arrangement of the components set forth in the following description or illustrated in the drawings.

The invention is capable of other embodiments or of being practiced or carried out in various ways. Also, it is to be understood that the phraseology and terminology employed herein is for the purpose of description and should not be regarded as limiting.

Reference is now made to FIG. 1A, which is a block diagram schematically illustrating a first apparatus for remote controlled physical activity monitoring, according to an exemplary embodiment of the present invention.

An exemplary apparatus 1000, according to an exemplary embodiment of the present invention, may be worn on a leg 100 of a user, say on a leg 100 of a user who is about to go biking or swimming.

For example, the apparatus 1000 may be worn on the leg 100, using a strap or a bracelet that parts of the apparatus 1000 may be fitted on.

The exemplary apparatus 1000 includes one or more sensors 101—say pressure meters (such as Force Sensing Resistors), orientation measurers (such as gyroscopic devices), etc., or any combination thereof, as described in further detail hereinbelow.

Optionally, the sensors 101 include one or more pairs of pressure meters that are arranged on the strap or bracelet, such that when the apparatus 1000 is worn by the user, each two pressure meters of a pair are deployed on opposite sides of a preferable area of the leg 100.

In one example, a pair of pressure meters is deployed on opposite sides of a muscle of the user's leg 100, say a first pressure meter 101 opposite a second pressure meter 101.

Optionally, the two pressure meters serve as control references for each other, as providers of complementary information, etc., as described in further detail hereinbelow.

Similarly, the sensors 101 may include one or more pairs of orientation measurers that are arranged on the strap or bracelet, such that when the apparatus 1000 is worn by the user, each two orientation measurers of a pair are deployed on preferable areas of the leg 100, say on areas positioned over opposite sides of the leg's 100 muscle.

In one example, the pair of orientation measurers 101 is positioned over opposite sides of the leg's upper muscle, say a first orientation measurer 101 opposite a second orientation measurer 101.

Optionally, the two orientation measurers serve as control references for each other, as providers of complementary information, etc., as described in further detail hereinbelow.

The apparatus 1000 further includes a computer processor 103, connected to the sensors 101, which is configured by programming, to derive monitoring control data from the sensors' 101 measurements, as described in further detail hereinbelow.

The computer processor 103 may include, but is not limited to: a microprocessor, a microcontroller (typically having a processing unit as well as a fixed amount of RAM, ROM and other peripherals, embedded on a single chip), or any other hardware component (say an integrated circuit) capable of performing calculations based on the measurements.

The apparatus 1000 further includes a data transmitter 104 connected to the computer processor 103.

The data transmitter 104 transmits the derived monitoring control data, over a wireless (say Bluetooth®) connection or over a wired connection, to a physical activity monitoring device (not shown).

The physical activity monitoring device may include one or more hardware and/or software components.

The components may include, but are not limited to: a camera—for capturing stills and/or video images of the user, a controller, a microphone—for capturing audio signals (say for allowing the user to vocally comment on events, in real time, during the physical activity), etc., or any combination thereof.

The components may alternatively or additionally include a stopwatch, a timer, a data storage (say a flash memory), a software module for analyzing body movement, a cellular modem (say for forwarding the images and vocal comments, live to a remote computer), etc., or any combination thereof.

Consequently, by moving the leg 100 in a way (say a direction, angle, etc.) predefined, say by a programmer of the apparatus 1000, the user may control the monitoring of the physical activity of the user, in real time (or in near real time), by the physical activity monitoring device.

Thus, in one example, when swimming in a pool, a user wearing the apparatus 1000 around one of the user's legs 100, may be allowed to control a physical activity monitoring device in a hands free manner.

In the example, the physical activity monitoring device includes a video camera installed besides the pool, and a controller (say a controller implemented as an electric circuit and/or a microchip, as known in the art).

The controller controls the camera and is in wireless communication with the apparatus' 1000 data transmitter 104, as described in further detail hereinabove.

In the example, when the user moves the leg in a certain way (say once to the right, and twice to the left), those left and right movements are sensed by the orientation measurers 101, which continuously measure the movements of the leg 100 wearing the device 1000.

Then, based on the leg's 100 movements measured by the orientation measurers 101, and as predefined—say by a programmer of the computer processor 103, the computer processor 103 derives monitoring control data. The monitoring control data includes operational data—namely, an instruction for the controller, to initiate a zoom-in and image capture operation of the camera.

Then, the data transmitter 104 transmits the derived monitoring control data to the controller.

Upon receipt of the instruction, the controller immediately actuates the video camera to zoom in on the user, and capture an image of the user, in real time (or near real time), exactly when the user makes that movement—say for capturing the user's jump into the pool.

In the example, the controller further includes a stopwatch, and the monitoring control data derived by the computer processor 103 based on the measured leg movements, further includes an instruction for the controller to start a time measurement of the user's swimming by the stopwatch.

Subsequently, the user moves the leg in a certain other way (say three times to the left), and those left movements are measured by the orientation measurers 101.

Then, based on the leg's 100 left movements measured by the orientation measurers 101, the computer processor 103 derives monitoring control data which includes operational data—namely, an instruction for the controller, to immediately stop the stopwatch and record the time thus measured by the stopwatch.

Then, the data transmitter 104 transmits the derived monitoring control data to the controller, which stops the stopwatch and records the time thus measured by the stopwatch, say in a flash memory attached to the controller.

Figure 1B:
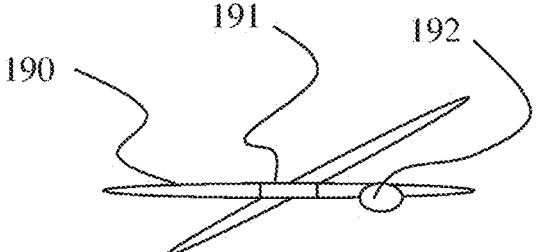
FIG. 1B is a block diagram schematically illustrating a second apparatus for remote controlled physical activity monitoring, according to an exemplary embodiment of the present invention.
Figure 1B:
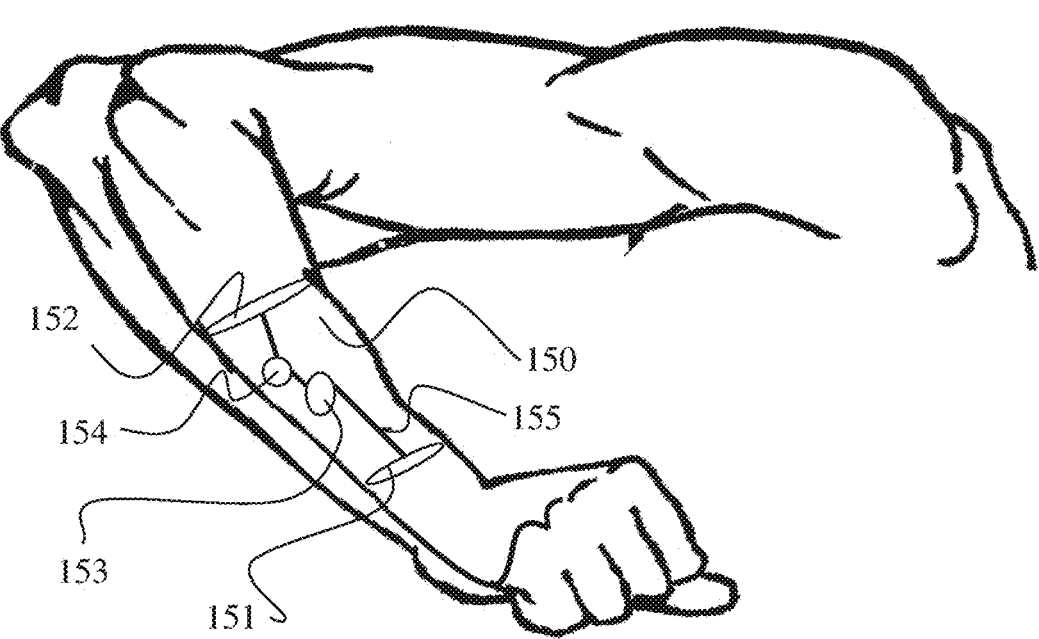

Reference is now made to FIG. 1B, which is a block diagram schematically illustrating a second apparatus for remote controlled physical activity monitoring, according to an exemplary embodiment of the present invention.

A second apparatus according to one exemplary embodiment of the present invention, is worn on a user's arm 150.

In one example, the second apparatus is embedded in a shirt worn on by a user, such that when the user wears the shirt, the apparatus components 151-154 are deployed on the user's arm 150. The components 151-154 are connected by an electrically circuit 155 which is implemented using conductive fibers embedded in the shirt—say using thin metal strands woven into the construction of the shirt's textile.

The apparatus includes one or more sensors, say a pressure meter 152—such as a Force Sensing Resistor (FSR), an orientation measurer 151—such as a gyroscopic device, a GPS Receiver, a Differential GPS Receiver, etc., or any combination thereof, as described in further detail hereinbelow.

Optionally, the sensors include one or more pairs of pressure meters 152 which are arranged on the shirt, such that when the shirt is worn by the user, each two pressure meters 152 of a pair are deployed on opposite sides of a preferable area of the user's arm 150.

In one example, a pair of pressure meters 152 is positioned over opposite sides of the arm 150, say on areas positioned over opposite sides of the arm's 150 muscle, as described in further detail hereinbelow.

Optionally, the two pressure meters 152 serve as control references for each other, as providers of complementary information, etc., as described in further detail hereinbelow.

Similarly, the sensors may include one or more pairs of orientation measurers 151 that are arranged on the shirt, such that when the shirt is worn by the user, each two orientation measurers 151 of a pair are deployed on preferable areas of the arm 150, say on areas positioned over opposite sides of the arm's 150 muscle.

Optionally, the two orientation measurers 151 serve as control references for each other, as providers of complementary information, etc., as described in further detail hereinbelow.

The apparatus embedded in the shirt, further includes a computer processor 153, connected to the sensors.

The computer processor 153 is also embedded in the shirt, and is configured by programming, to derive monitoring control data from the measurements, as described in further detail hereinbelow.

The computer processor 153 may include, but is not limited to: a microprocessor, a microcontroller (typically having a processing unit as well as a fixed amount of RAM, ROM and other peripherals, embedded on a single chip), or any other hardware component (say an integrated circuit) capable on performing calculations based on the measurements.

The apparatus further includes a data transmitter 154 also embedded in the shirt. The data transmitter 154 is connected to the computer processor 153, say by the electrical circuit 155 which is implemented using conductive fibers embedded in the shirt.

The data transmitter 154 transmits the derived control data, over a wireless (say Bluetooth®) connection or over a wired connection, to a physical activity monitoring device (not shown in FIG. 1B).

The physical activity monitoring device may include one or more hardware and/or software components.

In one example, the physical activity monitoring device includes a vehicle 190, say an aerial vehicle 190 such a quadcopter. In the example, the apparatus further includes a controller 191 deployed on the vehicle 190, for controlling the movement of the vehicle 190—say as a programmed microchip 191 which controls the aerial vehicle's 190 rotor engines, wings, etc., as known in the art.

The controller 191 maneuvers the vehicle 190 based on the monitoring control data wirelessly transmitted to the controller 191, by the data transmitter 154, say over a Radio Frequency (RF) Channel, as known in the art.

In the example, the physical activity monitoring device further includes other components.

The other components may include, but are not limited to: a camera 192—for capturing stills and/or video images of the user, a microphone—for capturing audio signals (say for allowing the user to vocally comment on events, in real time, during the physical activity), etc., or any combination thereof.

The components of the physical activity monitoring device may alternatively or additionally include a stop-watch, a timer, a data storage (say a flash memory), a cellular modem (say for forwarding the images and vocal comments, live to a remote computer), etc., or any combination thereof.

Optionally, the exemplary apparatus further includes one or more software modules such as a module for analyzing the user's body movement. Each one of the software modules may be implemented on the controller 191, on the computer processor 153 embedded on the user's shirt, on a remote computer to which the controller 191 forwards the images, etc.

Consequently, by moving his arm 150 in a specific way (say in a direction, angle, etc.) as predefined, say by a programmer of the apparatus, the user may control the physical activity monitoring device, using instructions transmitted to the controller 191, upon that arm's 150 movement.

Thus, in one example, a user rafting in a canoe, and wearing a suit in which an apparatus with the above described pressure meter 152, orientation measurer 151, computer processor 153 and data transmitter 154, are embedded, is allowed to control a physical activity monitoring device.

The physical activity monitoring device of the instant example, includes a quadcopter 190, a video camera 192, and a controller 191 which controls both the quadcopter 190 and the video camera 192, as described in further detail hereinabove.

In the example, pressure applied by the user's arm 150 muscle, as measured by the pressure meter 152, changes in the arm's 150 orientation, as measured by the orientation measurer 151, or both, are used by the user to control the physical activity monitoring device, even while the user's hands are busy rowing.

Further in the example, GPS data generated by the orientation measurer 151 and included in the monitoring control data transmitted to the controller 191, is used by the controller 191, to maneuver the quadcopter 190. The GPS data is used by the controller 191, to maneuver the quadcopter 190, so as to have the quadcopter 190 follow the rafting canoe, down a river, from above, as described in further detail hereinbelow.

In the example, throughout the rafting, both of the user's arms are busy rowing the canoe. However, when arriving at a certain segment of the river, the user spontaneously wishes to have the video camera 192 take video images, around the canoe.

To that end, the user changes the tension of the muscle of the user's arm 150—say by twice repeating a strengthening and weakening of the user's grip over the canoe's paddle, by changing the angle of the grip, etc.

The muscle tension changes are sensed by the pressure meter 152 which continuously measures the pressure applied by the muscle of the arm 150.

Then, based on the changes sensed by the pressure meter 152, the computer processor 153 derives monitoring control data which includes operational data—namely, an instruction for the controller 191, to initiate a zoom-in and image capture operation of the video camera 192 and to maneuver the quadcopter 190 so as to fly in a circle over the user.

In the example, the data transmitter 154 transmits the derived monitoring control data to the controller 191.

Upon receipt of the data which includes the instruction, the controller 191 immediately actuates the camera 192 to zoom in on the user, and controls the quadcopter's 190 rotor engines, so as to maneuver the quadcopter 190 to fly in a circle over the user.

Figure 2:
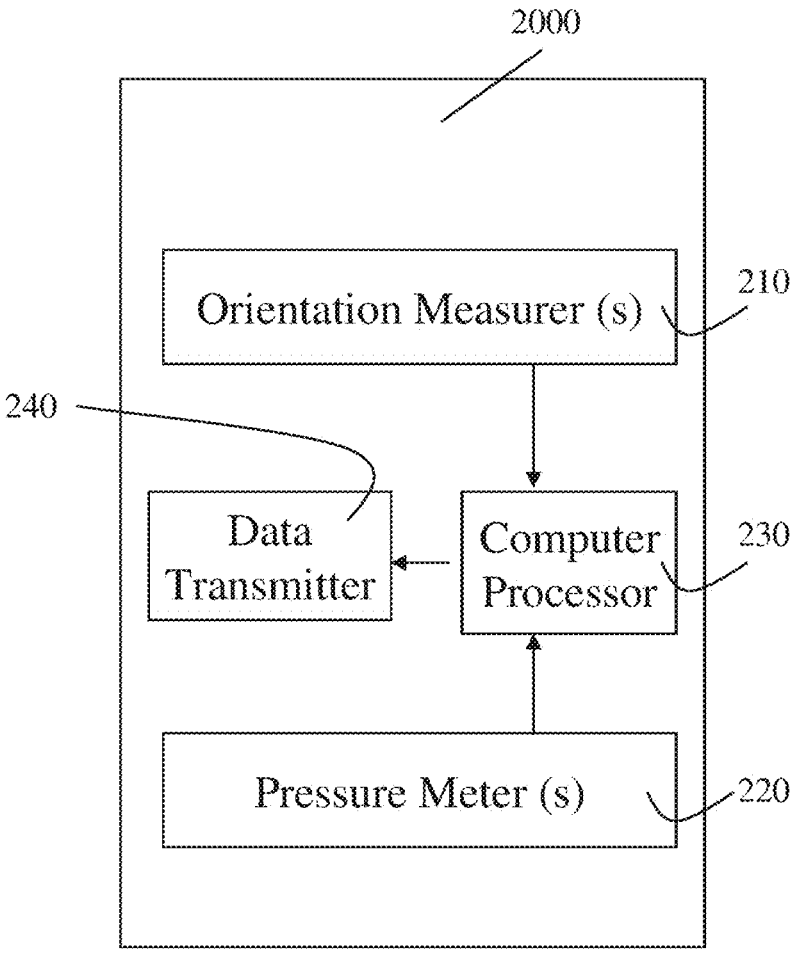
FIG. 2 is a block diagram schematically illustrating a third apparatus for remote controlled physical activity monitoring, according to an exemplary embodiment of the present invention.

Reference is now made to FIG. 2, which is a block diagram schematically illustrating a third apparatus for remote controlled physical activity monitoring, according to an exemplary embodiment of the present invention.

An exemplary apparatus 2000, according to one exemplary embodiment of the present invention, may be worn on one or more body parts of a user, as described in further detail hereinabove, and as illustrated, for example, in FIG. 1A, 1B.

The apparatus 2000 is used by the user, for remote controlling physical activity monitoring of the user by a physical activity monitoring device, as described in further detail hereinabove.

The apparatus 2000 includes one or more orientation measurers 210, wearable on one or more body parts of the user, say using a strap, bracelet, or shirt, on which the one or more orientation measurers 210 are arranged, as described in further detail hereinabove.

Each one of the orientation measurers 210 measures an orientation of the user's body part wearing the orientation measurer 210, during a physical activity of the user—say during skiing, rafting, swimming, diving, etc., as described in further detail hereinabove.

Each one of the orientation measurers 210 may include, but is not limited to one or more of: a gyroscope, a GPS (Global Positioning System) receiver, a Differential GPS (Global Positioning System) receiver, an accelerometer, an IMU (Inertial Measurement Unit), etc., as known in the art, or any combination thereof.

Optionally, one or more of the orientation measurers 210 measures angular orientation of the body part wearing the orientation measurer 210.

For example, the orientation measurer 210 may measure an angle of inclination of user's arm or leg, with respect to a preselected surface of reference. The measured angle may also be described as a rotation that would be needed to move the orientation measurer 210 from the surface into the orientation measurer's 210 angular position on the user's body part, as known in the art.

Optionally, one or more of the orientation measurers 210 measures bi-dimensional positional orientation of the orientation measurer 210, and hence of the body part wearing the orientation measurer 210. For example, the orientation measurer 210 may measure position of the orientation measurer's 210 projection on a preselected surface of reference, as known in the art.

Optionally, one or more of the orientation measurers 210 measures tri-dimensional positional orientation of the orientation measurer 210, and hence of the body part wearing the orientation measurer 210. For example, the orientation measurer 210 may measure the orientation measurer's 210 spatial position, with respect to a pre-defined three dimensional coordinate system, as known in the art.

Optionally, the orientation measurers 210 include one or more pairs of orientation measurers 210, arranged on the strap, bracelet, or shirt, such that when the strap, bracelet, or shirt, is worn by the user, each two orientation measurers 210 of a pair are deployed on preferable areas of the user's body part wearing the orientation measurers 210.

In one example, the pair of orientation measurers 210 is positioned over opposite sides of the muscle of the body part wearing the orientation measurers 210, say a first orientation measurer 210 opposite a second orientation measurer 210.

Optionally, the two orientation measurers 210 of each pair serve as control references for each other, as providers of complementary information (i.e. measurement), etc., as described in further detail hereinbelow.

The apparatus 2000 further includes one or more pressure meters 220, wearable on one or more body parts of a user, say using a strap, bracelet, or shirt, on which the one or more pressure meters 220 are arranged, as described in further detail hereinabove.

Each one of the pressure meters 220 measures pressure applied by muscle of the body part wearing the pressure meter 220.

Each one of the pressure meters 220 may include, but is not limited to one or more of; a conductive polymer based pressure sensor such as an FSR (Force Sensing Resistor), a capacitive-based pressure sensor, an electromagnetic sensor, etc., as known in the art, or any combination thereof.

Optionally, the pressure meters 220 include one or more pairs of pressure meters 220 that are arranged on the strap, bracelet, or shirt, such that when the strap, bracelet, or shirt is worn by the user, each two pressure meters 220 of a pair are deployed on preferable areas of the user's body part wearing that pair.

In one example, the pair of pressure meters 220 is positioned over opposite sides of the muscle of the body part wearing the pair of pressure meters 220, say a first pressure meter 220 opposite a second pressure meter 220.

The two pressure meters 220 of each pair may serve as control references for each other, as providers of complementary information (i.e. measurements), etc., as described in further detail hereinbelow.

The apparatus 2000 further includes a computer processor 230, in communication with the orientation measurers 210 and pressure meters 220.

The computer processor 230 may include, but is not limited to: a microprocessor, a microcontroller (typically having a processing unit as well as a fixed amount of RAM, ROM and other peripherals, embedded on a single chip), or any other hardware component (say an integrated circuit) capable on performing calculations based on the measured orientation and pressure.

The computer processor 230 is configured (say by programming), to derive monitoring control data from the measured orientation and pressure, as described in further detail hereinbelow.

Optionally, the computer processor 230 compares a measurement of a first one of the orientation measurers 210 with a measurement of a second one of the orientation measurers 210, for deriving the monitoring control data.

In one example, the computer processor 230 may use measurements of two orientation measurers 210 deployed on opposite sides of the body part wearing the orientation measurers 210, as control references of each other (say by verifying that the two measurements do not significantly differ from each other).

In a second example, the computer processor 230 may use measurements of two orientation measurers 210 deployed on opposite sides of the muscle of the body part wearing the orientation measurers 210, as complementary information, for deriving the control data.

For example, the computer processor 230 may use calculations based on measurements by both orientation measurers 210 of the pair, for deriving the monitoring control data.

Optionally, the calculations are of a change in angular orientation of a theoretical line which connects the two orientation measurers 210, with respect to a preselected surface of reference.

Similarly, the computer processor 230 may compare a measurement of a first one of the pressure meters 220 with a measurement of a second one of the pressure meters 220, for deriving the monitoring control data.

In one example, the computer processor 230 may use measurements of two pressure meters 220 deployed on opposite sides of a muscle of the body part wearing the pressure meters 220, as control references of each other (say by verifying that the two measurements do not significantly differ from each other).

In a second example, the computer processor 230 may use measurements of two pressure meters 220 deployed on opposite sides of a muscle of the body part wearing the pressure meters 220, as complementary information, for deriving the monitoring control data.

For example, the computer processor 230 may use calculations based on measurements by both pressure meters 220 of the pair, for deriving the monitoring control data.

The apparatus 2000 further includes a data transmitter 240, in communication with the computer processor 230.

The data transmitter 240 transmits the monitoring control data derived by the computer processor 230, to the physical activity monitoring device.

The physical activity monitoring device may include one or more hardware and/or software components.

In one example, the apparatus 2000 includes a physical activity monitoring (not shown in FIG. 2) device. The physical activity monitoring device includes a vehicle, say an aerial vehicle such a quadcopter, as described in further detail hereinabove, and as illustrated in FIG. 1B.

In the example, the physical activity monitoring device further includes a controller.

Optionally, the controller is implemented as one or more hardware components deployed on the vehicle, on the user's body, or on both—say a programmed microchip installed on the vehicle or as a remote control of the quadcopter, as known in the art.

The controller controls the movement of the vehicle, say by controlling the vehicle's rotor engines, wings, etc., as described in further detail hereinabove.

The controller maneuvers the vehicle based on the monitoring control data transmitted to the controller by the data transmitter 240.

The physical activity monitoring device of the example further includes other components.

The other components may include, but are not limited to: a camera—for capturing stills and/or video images of the user, a microphone—for capturing audio signals (say for allowing the user to vocally comment on events, in real time, during the physical activity), etc., or any combination thereof.

The components of the physical activity monitoring device may alternatively or additionally include a stop-watch, a timer, a data storage, a cellular modem—say for forwarding the images and vocal comments, live to a remote computer, etc., or any combination thereof.

Optionally, the apparatus 2000 further includes one or more software modules such as a module for analyzing the user's body movement, as known in the art. Each one of the software modules may be implemented on the controller, on the computer processor 230, on a computer in remote communication with the physical activity monitoring device, etc., as described in further detail hereinbelow.

Optionally, the data transmitter 240 transmits the monitoring control data to the physical activity monitoring device over a wired connection. For example, the data transmitter 240 may include an electric circuit that transmits the monitoring control data over wires. The wires may be connected to one of the physical activity monitoring device's USB (Universal Serial Bus) sockets, to a communications socket of a communications card installed on the physical activity monitoring device, etc., as known in the art.

Optionally, the data transmitter 240 transmits the monitoring control data to the physical activity monitoring device over a wireless connection. For example, the data transmitter 240 may include an electronic communications circuit that transmits the monitoring control data as radio-frequency (RF) signals, say in the Bluetooth® frequency range (2.400 GHz-2.480 GHz).

In a first example, the computer processor 230 derives the monitoring control data in a format which is already executable by a component of the physical activity monitoring device, say in a format already executable by a controller of a camera of the physical activity monitoring device, for actuating the camera to zoom in on the user.

In a second example, the computer processor 230 derives the monitoring control data in a format which is not ready for execution by the component of the physical activity monitoring device, say in a format which is not executable by the controller of the camera of the physical activity monitoring device.

However, in the second example, the apparatus 2000 further includes a data converter implemented as a computer program which runs on a computer processor of the physical activity monitoring device. Upon receipt of the monitoring control data, the computer program converts the received monitoring control data into a format executable by the camera's controller.

Stated differently, the computer processor 230 translates changes in pressure, orientation (or both), as measured by the pressure meters 220, and orientation measurers 210, respectively, into operational data (say instructions) included in the monitoring control data transmitted to the physical activity monitoring device.

The operational data causes the physical activity monitoring device to carry out operations of monitoring the user, as predefined for the specific measured changes—say to take an image of the user, to start a stopwatch, to maneuver a quadcopter into a position closer to the user, etc., as described in further detail hereinbelow.

In one example, the computer processor 230 translates a pressure change measured by one or more of the pressure meters 220, into the operational data included in the monitoring control data, as described in further detail hereinbelow.

In a second example, the computer processor 230 translates an angular orientation change measured by one or more of the orientation measurers 210, into the operational data included in the monitoring control data, as described in further detail hereinbelow.

In a third example, the computer processor 230 translates a movement in a predefined direction, measured by one or more of the orientation measurers 210, into the operational data included in the monitoring control data, as described in further detail hereinbelow.

Consequently, the apparatus 2000 may help the user to control the physical activity monitoring device, even if during the user's physical activity, the user's hands are busy (say busy holding to an axe during ice climbing, or busy rowing during rafting), as described in further detail hereinabove.

The apparatus 2000 may also include a power source (not shown), say one or more miniature batteries, as known in the art.

Figure 3:
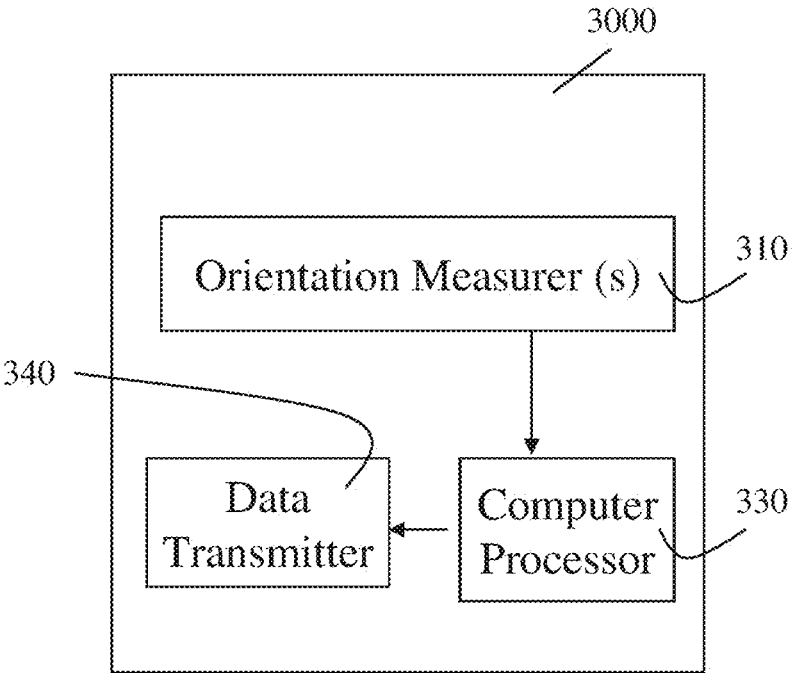
FIG. 3 is a block diagram schematically illustrating a fourth apparatus for remote controlled physical activity monitoring, according to an exemplary embodiment of the present invention.

Reference is now made to FIG. 3, which is a block diagram schematically illustrating a fourth apparatus for remote controlled physical activity monitoring, according to an exemplary embodiment of the present invention.

An exemplary apparatus 3000, according to an exemplary embodiment of the present invention, may be worn on one or more body parts of a user, as described in further detail hereinabove, and as illustrated, for example, in FIG. 1A, 1B.

The apparatus 3000 is used by the user, for remote controlling physical activity monitoring of the user by a physical activity monitoring device, as described in further detail hereinabove.

The apparatus 3000 includes one or more orientation measurers 310, wearable on one or more body parts of a user, say using a strap, bracelet, or shirt, on which the one or more orientation measurers 310 are arranged, as described in further detail hereinabove.

Each one of the orientation measurers 310 measures an orientation of the user's body part wearing the orientation measurer 310, during a physical activity of the user—say during skiing, rafting, swimming, diving, etc., as described in further detail hereinabove.

Each one of the orientation measurers 310 may include, but is not limited to one or more of: a gyroscope, a GPS (Global Positioning System) receiver, a Differential GPS (Global Positioning System) receiver, an accelerometer, an IMU (Inertial Measurement Unit), etc., as known in the art, or any combination thereof.

Optionally, one or more of the orientation measurers 310 measures angular orientation of the body part wearing the orientation measurer 310.

For example, the orientation measurer 310 may measure an angle of inclination of user's arm or leg, with respect to a preselected surface of reference. The measured angle may also be described as a rotation that would be needed to move the orientation measurer 310 from the surface to the angular position of the orientation measurer 310 on the user's body part, as known in the art.

Optionally, one or more of the orientation measurers 310 measures bi-dimensional positional orientation of the orientation measurer 310, and hence of the body part wearing the orientation measurer 310. For example, the orientation measurer 310 may measure position of the orientation measurer's 310 projection on a preselected surface of reference, as known in the art.

Optionally, one or more of the orientation measurers 310 measures tri-dimensional positional orientation of the orientation measurer 310, and hence of the body part wearing the orientation measurer 310. For example, the orientation measurer 310 may measure the orientation measurer's 310 spatial position with respect to a pre-defined three dimensional coordinate system, as known in the art.

Optionally, the orientation measurers 310 include one or more pairs of orientation measurers 310, arranged on the strap, bracelet, or shirt, such that when the strap, bracelet, or shirt, is worn by the user, each two orientation measurers 310 of a pair are deployed on preferable areas of the user's body part wearing the orientation measurers 310.

In one example, the pair of orientation measurers 310 is positioned over opposite sides of the muscle of the body part wearing the orientation measurers 310, say a first orientation measurer 310 opposite a second orientation measurer 310.

Optionally, the two orientation measurers 310 of each pair serve as control references for each other, as providers of complementary information (i.e. measurement), etc., as described in further detail hereinbelow.

The apparatus 3000 further includes a computer processor 330, in communication with the orientation measurers 310.

The computer processor 330 may include, but is not limited to: a microprocessor, a microcontroller (typically having a processing unit as well as a fixed amount of RAM, ROM and other peripherals, embedded on a single chip), or any other hardware component (say an integrated circuit) capable on performing calculations based on the orientation measured by the orientation measurers 310.

The computer processor 330 is configured (say by programming), to derive monitoring control data from the measured orientation, say from changes in the measured orientation, as described in further detail hereinbelow.

Optionally, the computer processor 330 compares a measurement of a first one of the orientation measurers 310 with a measurement of a second one of the orientation measurers 310, for deriving the monitoring control data.

In one example, the computer processor 330 may use measurements of two orientation measurers 310 deployed on opposite sides of the body part wearing the orientation measurers 310, as control references of each other (say by verifying that the two measurements do not significantly differ from each other).

In a second example, the computer processor 330 may use measurements of two orientation measurers 210 deployed on opposite sides of a muscle of the body part wearing the orientation measurers 310, as complementary information, for deriving the control data.

For example, the computer processor 330 may use calculations based on measurements by both orientation measurers 310 of the pair, for deriving the monitoring control data.

Optionally, the calculations are of a change in angular orientation of a theoretical line which connects the two orientation measurers 310, with respect to a preselected surface of reference.

The apparatus 2000 further includes a data transmitter 340, in communication with the computer processor 330.

The data transmitter 340 transmits the control data to the physical activity monitoring device.

The physical activity monitoring device may include one or more hardware and/or software components, as described in further detail hereinabove.

In one example, the apparatus 3000 includes a physical activity monitoring (not shown in FIG. 3) device. The physical activity monitoring device includes a vehicle, say an aerial vehicle such a quadcopter, as described in further detail hereinabove, and as illustrated in FIG. 1B.

In the example, the physical activity monitoring device further includes a controller, for controlling the movement of the vehicle—say a programmed microchip which controls the aerial vehicle's rotor engines, wings, etc., as described in further detail hereinabove.

The controller maneuvers the vehicle based on the monitoring control data wirelessly transmitted to the controller, by the data transmitter 340.

The physical activity monitoring device of the example further includes other components.

The other components may include, but are not limited to: a camera—for capturing stills and/or video images of the user, a microphone—for capturing audio signals (say for allowing the user to vocally comment on events, in real time, during the physical activity), etc., or any combination thereof.

The components of the physical activity monitoring device may alternatively or additionally include a stopwatch, a timer, a data storage, a cellular modem—say for forwarding the images and vocal comments, live to a remote computer, etc., or any combination thereof.

Optionally, the apparatus 3000 further includes one or more software modules such as a module for analyzing the user's body movement, as known in the art. Each one of the software modules may be implemented on the controller, on the computer processor 330, on a computer in remote communication with the physical activity monitoring device, etc., as described in further detail hereinbelow.

Optionally, the data transmitter 340 transmits the monitoring control data to the physical activity monitoring device over a wired connection. For example, the data transmitter 340 may include an electric circuit that transmits the monitoring control data over wires. The wires may be connected to one of the physical activity monitoring device's USB (Universal Serial Bus) sockets, to a communications socket of a communications card installed in the physical activity monitoring device, etc., as known in the art.

Optionally, the data transmitter 340 transmits the monitoring control data to the physical activity monitoring device over a wireless connection. For example, the data transmitter 340 may include an electronic communications circuit that transmits the monitoring control data as radio-frequency (RF) signals, say in the Bluetooth® frequency range (2.400 GHz-2.480 GHz).

In a first example, the computer processor 330 derives the monitoring control data in a format which is already executable by a component of the physical activity monitoring device, say in a format already executable by a controller of a camera of the physical activity monitoring device, for actuating the camera to zoom in on the user.

In a second example, the computer processor 330 derives the monitoring control data in a format which is not ready for execution by the component of the physical activity monitoring device, say in a format which is not executable by the controller of the camera of the physical activity monitoring device.

However, in the second example, the apparatus 3000 further includes a data converter implemented as a computer program which runs on a computer processor of the physical activity monitoring device. Upon receipt of the monitoring control data, the computer program converts the received monitoring control data into a format executable by the camera's controller.

Stated differently, the computer processor 330 translates changes in orientation, as measured by the orientation measurers 310, into operational data (say instructions) included in the monitoring control data, as described in further detail hereinabove.

The operational data causes the physical activity monitoring device to carry out operations of monitoring the user, as predefined for the specific measured changes—say to take an image of the user, to start a stopwatch, to maneuver a quadcopter into a position closer to the user, etc., as described in further detail hereinbelow.

In one example, the computer processor 330 translates an angular orientation change measured by one or more of the orientation measurers 310, into the operational data included in the monitoring control data, as described in further detail hereinbelow.

In a second example, the computer processor 330 translates a movement in a predefined direction, measured by one or more of the orientation measurers 310, into the operational data included in the monitoring control data, as described in further detail hereinbelow.

Consequently, the apparatus 3000 may help the user to control the physical activity monitoring device, even if during the user's physical activity, the user's hands are busy, as described in further detail hereinabove.

The apparatus 3000 may further include a power source (not shown), say one or more miniature batteries, as known in the art.

Figure 4:
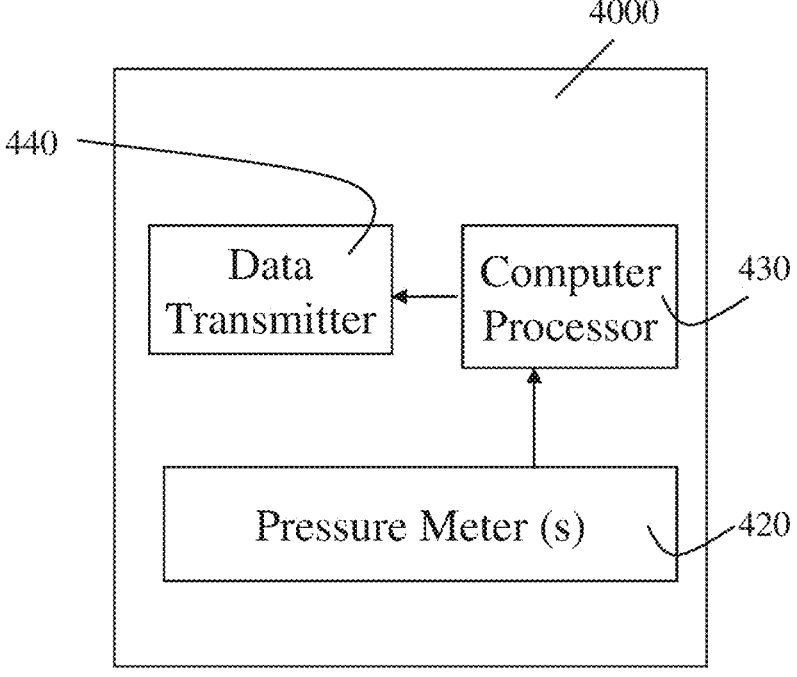
FIG. 4 is a block diagram schematically illustrating a fifth apparatus for remote controlled physical activity monitoring, according to an exemplary embodiment of the present invention.

Reference is now made to FIG. 4, which a block diagram schematically illustrating a fifth apparatus for remote controlled physical activity monitoring, according to an exemplary embodiment of the present invention.

An exemplary apparatus 4000, according to an exemplary embodiment of the present invention, may be worn on one or more body parts of a user, as described in further detail hereinabove, and as illustrated, for example, in FIG. 1A, 1B.

The apparatus 4000 is used by the user, for remote controlling physical activity monitoring of the user by a physical activity monitoring device, as described in further detail hereinabove.

The apparatus 4000 includes one or more pressure meters 420, wearable on one or more body parts of a user, say using a strap, bracelet, or shirt, on which the one or more pressure meters 420 are arranged, as described in further detail hereinabove.

Each one of the pressure meters 420 measures pressure applied by a muscle of the body part wearing the pressure meter 420.

Each one of the pressure meters 420 may include, but is not limited to one or more of: a conductive polymer based pressure sensor such as an FSR (Force Sensing Resistor), a capacitive-based pressure sensor, an electromagnetic sensor, etc., as known in the art, or any combination thereof.

Optionally, the pressure meters 420 include one or more pairs of pressure meters 420 which are arranged on the strap, bracelet, or shirt, such that when the strap, bracelet, or shirt is worn by the user, each two pressure meters 420 of a pair are deployed on preferable areas of the user's body part wearing that pair.

In one example, the pair of pressure meters 420 is positioned over opposite sides of a muscle of the body part wearing the pair of pressure meters 420, say a first pressure meter 420 opposite a second pressure meter 420.

The two pressure meters 420 of each pair may serve as control references for each other, as providers of complementary information (i.e. measurements), etc., as described in further detail hereinbelow.

The apparatus 4000 further includes a computer processor 430, in communication with the pressure meters 420.

The computer processor 430 may include, but is not limited to: a microprocessor, a microcontroller (typically having a processing unit as well as a fixed amount of RAM, ROM and other peripherals, embedded on a single chip), or any other hardware component (say an integrated circuit) capable on performing calculations based on the measured orientations and pressures.

The computer processor 430 is configured (say by programming), to derive monitoring control data from the measured pressure, as described in further detail hereinbelow.

In a first example, the computer processor 430 may use measurements of two pressure meters 420 deployed on opposite sides of a muscle of the body part wearing the pressure meters 420, as control references of each other (say by verifying that the two measurements do not significantly differ from each other).

In a second example, the computer processor 430 may use measurements of two pressure meters 420 deployed on opposite sides of the muscle of the body part wearing the pressure meters 420, as complementary information, for deriving the monitoring control data.

For example, the computer processor 430 may use calculations based on measurements by both pressure meters 420 of the pair, for deriving the monitoring control data.

The apparatus 4000 further includes a data transmitter 440, in communication with the computer processor 430.

The data transmitter 440 transmits the control data to the physical activity monitoring device.

The physical activity monitoring device may include one or more hardware and/or software components, as described in further detail hereinabove.

In one example, the apparatus 4000 includes a physical activity monitoring (not shown in FIG. 4) device. The physical activity monitoring device includes a vehicle, say an aerial vehicle such a quadcopter, as described in further detail hereinabove, and as illustrated in FIG. 1B.

In the example the physical activity monitoring device further includes a controller, for controlling the movement of the vehicle—say a programmed microchip which controls the aerial vehicle's rotor engines, wings, etc., as described in further detail hereinabove.

The controller maneuvers the vehicle based on the monitoring control data wirelessly transmitted to the controller, by the data transmitter 440, as described in further detail hereinabove.

The physical activity monitoring device of the example further includes other components.

The other components may include, but are not limited to: a camera—for capturing stills and/or video images of the user, a microphone—for capturing audio signals (say for allowing the user to vocally comment on events, in real time, during the physical activity), etc., or any combination thereof.

The components of the physical activity monitoring device may alternatively or additionally include a stopwatch, a timer, a data storage, a cellular modem—say for forwarding the images and vocal comments, live to a remote computer, etc., or any combination thereof.

Optionally, the apparatus 4000 further includes one or more software modules such as a module for analyzing the user's body movement, as known in the art. Each one of the software modules may be implemented on the controller, on the computer processor 430, on a computer in remote communication with the physical activity monitoring device, etc., as described in further detail hereinbelow.

Optionally, the data transmitter 440 transmits the monitoring control data to the physical activity monitoring device over a wired connection. For example, the data transmitter 440 may include an electric circuit that transmits the monitoring control data over wires. The wires may be connected to one of the physical activity monitoring device's USB (Universal Serial Bus) sockets, to a communications socket of a communications card installed in the physical activity monitoring device, etc., as known in the art.

Optionally, the data transmitter 440 transmits the monitoring control data to the physical activity monitoring device over a wireless connection. For example, the data transmitter

440 may include an electronic communications circuit that transmits the monitoring control data as radio-frequency (RF) signals, say in the Bluetooth® frequency range (2.400 GHz-2.480 GHz).

In a first example, the computer processor 430 derives the monitoring control data in a format which is already executable by a component of the physical activity monitoring device, say in a format already executable by a controller of a camera of the physical activity monitoring device, for actuating the camera to zoom in on the user.

In a second example, the computer processor 430 derives the monitoring control data in a format which is not ready for execution by the component of the physical activity monitoring device, say in a format which is not executable by the controller of a camera of the physical activity monitoring device.

However, in the second example, the apparatus 4000 further includes a data converter implemented as a computer program which runs on a computer processor of the physical activity monitoring device. Upon receipt of the monitoring control data, the computer program converts the received monitoring control data into a format executable by the camera's controller.

Stated differently, the computer processor 430 translates changes in pressure, as measured by the pressure meters 420, into operational data (say instructions) included in the monitoring control data, as described in further detail hereinabove.

The operational data causes the physical activity monitoring device to carry out operations of monitoring the user, as predefined for the specific measured changes—say to take an image of the user, to start a stopwatch, to maneuver a quadcopter into a position closer to the user, etc., as described in further detail hereinbelow.

Consequently, the apparatus 4000 may help the user to control the physical activity monitoring device, even if during the user's physical activity, the user's hands are busy (say busy holding to an axe during ice climbing, or rowing during rafting), as described in further detail hereinabove.

The apparatus 4000 may further include a power source (not shown), say one or more miniature batteries, as known in the art.

Figure 5:
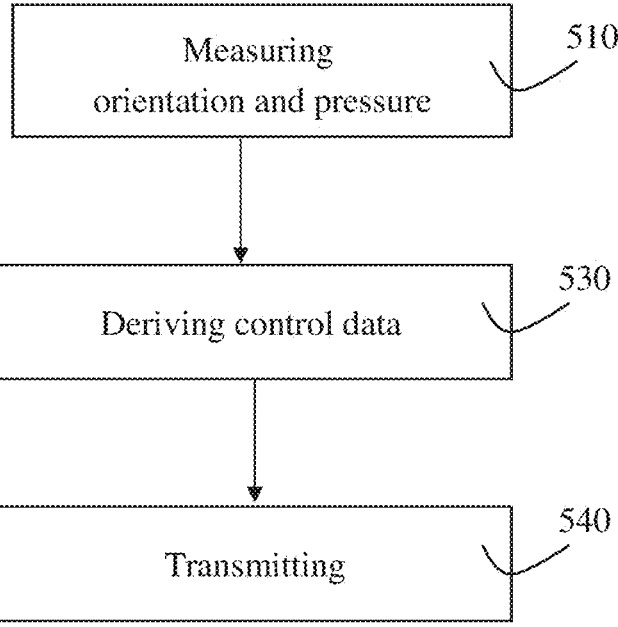
FIG. 5 is a flowchart illustrating a first method for remote controlled physical activity monitoring, according to an exemplary embodiment of the present invention.

Reference is now made to FIG. 5, which is a flowchart illustrating a first method for remote controlled physical activity monitoring, according to an exemplary embodiment of the present invention.

In a first exemplary method, according to an exemplary embodiment of the present invention, during a physical activity—such as swimming, canoe rafting, skiing, etc., a user may remotely control a monitoring of the user's physical activity, even when the user's hands are busy, as described in further detail hereinabove.

In the exemplary method, the user wears an apparatus, say apparatus 2000, on one or more body parts of a user, as described in further detail hereinabove, and as illustrated, for example, in FIG. 1A, 1B.

The apparatus 2000 is used by the user, for remote controlling a physical activity monitoring of the user by a physical activity monitoring device, as described in further detail hereinabove.

In the method, there are measured 510 orientations of one or more body parts of the user, say using the orientation measurers 210 of apparatus 2000, which are worn by the user during a physical activity of the user—say during skiing, rafting, swimming, etc. as described in further detail hereinabove.

Optionally, in the method, there is measured 510 an angular orientation of the body part wearing the orientation measurer 210.

For example, one or more of the orientation measurers 210 may measure 510 an angle of inclination of user's arm or leg, with respect to a preselected surface of reference. The measured 510 angle may also be described as a rotation that would be needed to move the orientation measurer 210 from the surface to the angular position of the orientation measurer 210 on the user's body part, as known in the art.

Optionally, in the method, there is measured 510 a bi-dimensional positional orientation of the orientation measurer 210, and hence of the body part wearing the orientation measurer 210. For example, the orientation measurer 210 may measure 510 position of a projection of the orientation measurer's 210 on a preselected surface of reference, as known in the art.

Optionally, in the method, there is measured 510 a tri-dimensional positional orientation of the orientation measurer 210, and hence of the body part wearing the orientation measurer 210. For example, the orientation measurer 210 may measure 510 the orientation measurer's 210 spatial position, with respect to a pre-defined three dimensional coordinate system, as known in the art.

Optionally, the orientation measurers 210 include one or more pairs of orientation measurers 210, arranged on the strap, bracelet, or shirt, such that when the strap, bracelet, or shirt, is worn by the user, each two orientation measurers 210 of a pair are deployed on preferable areas of the user's body part wearing the orientation measurers 210.

In one example, the pair of orientation measurers 210 is positioned over opposite sides of a muscle of the body part wearing the orientation measurers 210, say a first orientation measurer 210 opposite a second orientation measurer 210, as described in further detail hereinabove.

Optionally, in the method, the two orientation measurers 210 of each pair serve as control references for each other, as providers of complementary information (i.e. measurement), etc., as described in further detail hereinabove.

In the method, there is measured 510 pressure applied by muscle of one or more body parts of the user, say using the pressure meters 220 of apparatus 2000.

Optionally, the pressure meters 220 include one or more pairs of pressure meters 220 that are arranged on the strap, bracelet, or shirt, such that when the strap, bracelet, or shirt is worn by the user, each two pressure meters 220 of a pair are deployed on preferable areas of the user's body part wearing that pair.

In one example, the pair of pressure meters 220 is positioned over opposite sides of a muscle of the body part wearing the pair of pressure meters 220, say a first pressure meter 220 opposite a second pressure meter 220, as described in further detail hereinabove.

The two pressure meters 220 of each pair may serve as control references for each other, as providers of complementary information (i.e. measurements), etc., as described in further detail hereinbelow.

Next, there is derived 530 monitoring control data from the measured 510 orientation and pressure, say by the computer processor 230 of apparatus 2000, as described in further detail hereinabove.

Optionally, in the method, there is further compared a measurement 510 of a first one of the orientation measurers 210 with a measurement 510 of a second one of the orientation measurers 210, for deriving 530 the monitoring control data.

In one example, there may be used measurements 510 of two orientation measurers 210 deployed on opposite sides of the body part wearing the orientation measurers 210, as control references of each other (say by verifying that the two measurements 510 do not significantly differ from each other), for deriving 530 the monitoring control data.

In a second example, there may be used measurements 510 of two orientation measurers 210 deployed on opposite sides of the body part wearing the orientation measurers 210, as complementary information, for deriving 530 the monitoring control data.

For example, the computer processor 230 may use calculations based on measurements 510 by both orientation measurers 210 of the pair, for deriving 530 the monitoring control data.

Optionally, the calculations are of a change in angular orientation of a theoretical line which connects the two orientation measurers 210, with respect to a preselected surface of reference.

Similarly, there may be compared a measurement 510 of a first one of the pressure meters 220 with a measurement 510 of a second one of the pressure meters 220, for deriving 530 the monitoring control data.

In one example, the computer processor 230 may use measurements 510 of two pressure meters 220 deployed on opposite sides of the muscle of the body part wearing the pressure meters 220, as control references of each other (say by verifying that the two measurements 510 do not significantly differ from each other), for deriving 530 the monitoring control data.

In a second example, the computer processor 230 may use measurements 510 of two pressure meters 220 deployed on opposite sides of a muscle of the body part wearing the pressure meters 220, as complementary information, for deriving 530 the monitoring control data.

For example, the computer processor 230 may use calculations based on measurements 510 by both pressure meters 220 of the pair, for deriving 530 the monitoring control data.

Then, the monitoring control data is transmitted 540 to the physical activity monitoring device, so as to control a monitoring of the user's physical activity, as described in further detail hereinabove.

On the physical activity monitoring device, there are carried out steps of monitoring the user's physical activity, based on the monitoring control data, in real time or near real time.

The steps may include, but are not limited: a step of capturing a stills image of the user with a camera, a step of starting a stopwatch, a step of capturing and recording a vocal comment of the user, a step of moving the physical activity monitoring device into a position closer to the user, etc., as described in further detail hereinabove.

The physical activity monitoring device may include one or more hardware and/or software components, say an aerial vehicle such a quadcopter, a controller which controls the movement of the vehicle—say a remote control or a programmed microchip which controls the aerial vehicle's rotor engines, wings, etc., as described in further detail hereinabove.

The physical activity monitoring device may further include other components. The other components may include, but are not limited to: a camera—for capturing stills and/or video images of the user, a microphone—say for allowing the user to vocally comment on events, in real time, during the physical activity, etc., or any combination thereof.

The components of the physical activity monitoring device may alternatively or additionally include a stopwatch, a timer, a data storage, a cellular modem—say for forwarding the images and vocal comments, live to a remote computer, etc., or any combination thereof.

In one example, the physical activity monitoring device includes an aerial vehicle which carries a camera and a controller. Based on the monitoring control data, the controller control the vehicle's engines, so as to maneuver the aerial vehicle, and operates the camera, as described in further detail hereinabove.

Optionally, the method further includes analyzing the user's body movement based on images captured by the camera, say using a software module implemented on the physical activity monitoring device, on a computer in remote communication with the physical activity monitoring device, etc., as described in further detail hereinbelow.

Optionally, the monitoring control data is transmitted 540 to the physical activity monitoring device over a wired connection. For example, the monitoring control data may be transmitted 540 over wires, or rather wirelessly, say as radio-frequency (RF) signals in the Bluetooth® frequency range (2.400 GHz-2.480 GHz).

In a first example, the monitoring control data are derived 530 in a format which is already executable by a component of the physical activity monitoring device, say in a format already executable by the controller of a camera of the physical activity monitoring device, for actuating the camera to zoom in on the user.

In a second example, the monitoring control data are derived 530 in a format which is not yet ready for execution by the component of the physical activity monitoring device, say in a format which is not executable by a controller of the camera of the physical activity monitoring device.

However, in the second example, the method further includes a step of conversion by a computer program which runs on a computer processor of the physical activity monitoring device. Upon receipt of the monitoring control data, the computer program converts the received monitoring control data into a format executable by the camera's controller.

Stated differently, with the exemplary method, measured 510 changes in pressure, orientation (or both the measured 150 pressure and the measured 150 orientation) are converted into operational data (say instructions) included in the monitoring control data.

The operational data causes the physical activity monitoring device to carry out operations of monitoring the user, as predefined for the specific measured 510 changes—say to take an image of the user, to start a stopwatch, to maneuver a quadcopter into a position closer to the user, etc.

In one example, there is translated a pressure change measured by one or more of the pressure meters 220, into the operational data included in the monitoring control data, as described in further detail hereinbelow.

In a second example, there is translated an angular orientation change measured by one or more of the orientation measurers 210, into the operational data included in the monitoring control data, as described in further detail hereinbelow.

In a third example, there is translated a movement in a predefined direction, measured by one or more of the orientation measurers 210, into the operational data included in the monitoring control data, as described in further detail hereinbelow.

Consequently, the user is allowed to control the physical activity monitoring device, even if during the user's physical activity, the user's hands are busy (say busy holding to an axe during ice climbing, or busy rowing during rafting), as described in further detail hereinabove.

Figure 6:
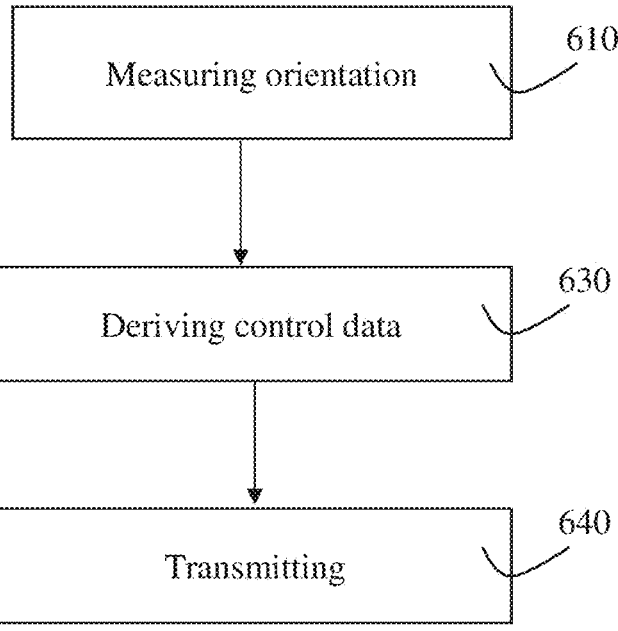
FIG. 6 is a flowchart illustrating a second method for remote controlled physical activity monitoring, according to an exemplary embodiment of the present invention.

Reference is now made to FIG. 6, which is a flowchart illustrating a second method for remote controlled physical activity monitoring, according to an exemplary embodiment of the present invention.

In a second exemplary method, according to an exemplary embodiment of the present invention, during a physical activity—such as swimming, canoe rafting, skiing, etc., a user may remotely control a monitoring of the user's physical activity, even when the user's hands are busy, as described in further detail hereinabove.

In the exemplary method, the user wears an apparatus, say apparatus 3000, on one or more body parts of a user, as described in further detail hereinabove, and as illustrated, for example, in FIG. 1A, 1B.

The apparatus 3000 is used by the user, for remote controlling a physical activity monitoring of the user by a physical activity monitoring device, as described in further detail hereinabove.

In the method, there are measured 610 orientations of one or more body parts of the user, say using the orientation measurers 310 of apparatus 3000, which are worn by the user during a physical activity of the user—say during skiing, rafting, swimming, etc. as described in further detail hereinabove.

Optionally, in the method, there is measured 610 an angular orientation of the body part wearing the orientation measurer 310.

For example, one or more of the orientation measurers 310 may measure 610 an angle of inclination of user's arm or leg, with respect to a preselected surface of reference. The measured 610 angle may also be described as a rotation that would be needed to move the orientation measurer 310 from the surface to the angular position of the orientation measurer 310 on the user's body part, as known in the art.

Optionally, in the method, there is measured 610 a bi-dimensional positional orientation of the orientation measurer 310, and hence of the body part wearing the orientation measurer 310. For example, the orientation measurer 310 may measure 610 position of a projection of the orientation measurer's 310 on a preselected surface of reference, as known in the art.

Optionally, in the method, there is measured 610 a tri-dimensional positional orientation of the orientation measurer 310, and hence of the body part wearing the orientation measurer 310. For example, the orientation measurer 310 may measure 610 the orientation measurer's 310 spatial position, with respect to a pre-defined three dimensional coordinate system, as known in the art.

Optionally, the orientation measurers 310 include one or more pairs of orientation measurers 310, arranged on the strap, bracelet, or shirt, such that when the strap, bracelet, or shirt, is worn by the user, each two orientation measurers 310 of a pair are deployed on preferable areas of the user's body part wearing the orientation measurers 310.

In one example, the pair of orientation measurers 310 is positioned over opposite sides of the a of the body part wearing the orientation measurers 310, say a first orientation measurer 310 opposite a second orientation measurer 310.

Optionally, in the method, the two orientation measurers 310 of each pair serve as control references for each other, as providers of complementary information (i.e. measurement), etc., as described in further detail hereinbelow.

Next, there is derived 630 monitoring control data from the measured 610 orientation, say by the computer processor 330 of apparatus 3000, as described in further detail hereinabove.

Optionally, in the method, there is further compared a measurement 610 of a first one of the orientation measurers 310 with a measurement 610 of a second one of the orientation measurers 310, for deriving 630 the monitoring control data.

In one example, there may be used measurements 610 of two orientation measurers 310 deployed on opposite sides of the body part wearing the orientation measurers 310, as control references of each other (say by verifying that the two measurements 610 do not significantly differ from each other), for deriving 630 the monitoring control data.

In a second example, there may be used measurements 610 of two orientation measurers 310 deployed on opposite sides of the body part wearing the orientation measurers 310, as complementary information, for deriving 630 the monitoring control data.

For example, the computer processor 330 may use calculations based on measurements 610 by both orientation measurers 310 of the pair, for deriving 630 the monitoring control data.

Optionally, the calculations are of a change in angular orientation of a theoretical line which connects the two orientation measurers 310, with respect to a preselected surface of reference.

Then, the derived 630 monitoring control data is transmitted 640 to the physical activity monitoring device, so as to control a monitoring of the user's physical activity, as described in further detail hereinabove.

On the physical activity monitoring device, there are carried out steps of monitoring the user's physical activity, based on the monitoring control data, in real time or near real time.

The steps may include, but are not limited: a step of capturing a stills image of the user with a camera, a step of starting a stopwatch, a step of capturing and recording a vocal comment of the user, a step of moving the physical activity monitoring device into a position closer to the user, etc., as described in further detail hereinabove.

The physical activity monitoring device may include one or more hardware and/or software components, say an aerial vehicle such a quadcopter, a controller which controls the movement of the vehicle—say a programmed microchip which controls the aerial vehicle's rotor engines, wings, etc., as described in further detail hereinabove.

The physical activity monitoring device of the may further include other components, such as: a camera—for capturing stills and/or video images of the user, a microphone—say for allowing the user to vocally comment on events, in real time, during the physical activity, etc., or any combination thereof.

The components of the physical activity monitoring device may alternatively or additionally include a stopwatch, a timer, a data storage, a cellular modem—say for forwarding the images and vocal comments, live to a remote computer, etc., or any combination thereof.

In one example, the physical activity monitoring device includes an aerial vehicle which carries a camera and a controller. Based on the monitoring control data, the controller control the vehicle's engines, so as to maneuver the aerial vehicle, and operates the camera, as described in further detail hereinabove.

Optionally, the method further includes analyzing the user's body movement based on images captured by the camera, say using a software module implemented on the physical activity monitoring device, on a computer in remote communication with the physical activity monitoring device, etc., as described in further detail hereinbelow.

Optionally, the monitoring control data is transmitted 640 to the physical activity monitoring device over a wired connection. For example, the monitoring control data may be transmitted 640 over wires, or rather wirelessly, say as radio-frequency (RF) signals in the Bluetooth® frequency range (2.400 GHz-2.480 GHz).

In a first example, the monitoring control data are derived 630 in a format which is already executable by a component of the physical activity monitoring device, say in a format already executable by a controller of a camera of the physical activity monitoring device, for actuating the camera to zoom in on the user.

In a second example, the monitoring control data are derived 630 in a format which is not yet ready for execution by the component of the physical activity monitoring device, say in a format which is not executable by the controller of the camera of the physical activity monitoring device.

However, in the second example, the method further includes a step of conversion by a computer program which runs on a computer processor of the physical activity monitoring device. Upon receipt of the monitoring control data, the computer program converts the received monitoring control data into a format executable by the camera's controller.

Stated differently, with the exemplary method, measured 610 changes in the orientation are converted into operational data (say instructions) included in the monitoring control data.

The operational data causes the physical activity monitoring device to carry out operations of monitoring the user, as predefined for the specific measured 610 changes—say to take an image of the user, to start a stopwatch, to maneuver a quadcopter into a position closer to the user, etc.

In one example, there is translated an angular orientation change measured 610 by one or more of the orientation measurers 310, into the operational data included in the monitoring control data, as described in further detail hereinbelow.

In a second example, there is translated a movement in a predefined direction, measured 610 by one or more of the orientation measurers 310, into the operational data included in the monitoring control data, as described in further detail hereinbelow.

Consequently, the user is allowed to control the physical activity monitoring device, even if during the user's physical activity, the user's hands are busy (say busy holding to an axe during ice climbing, busy rowing during rafting, etc.), as described in further detail hereinabove.

Figure 7:
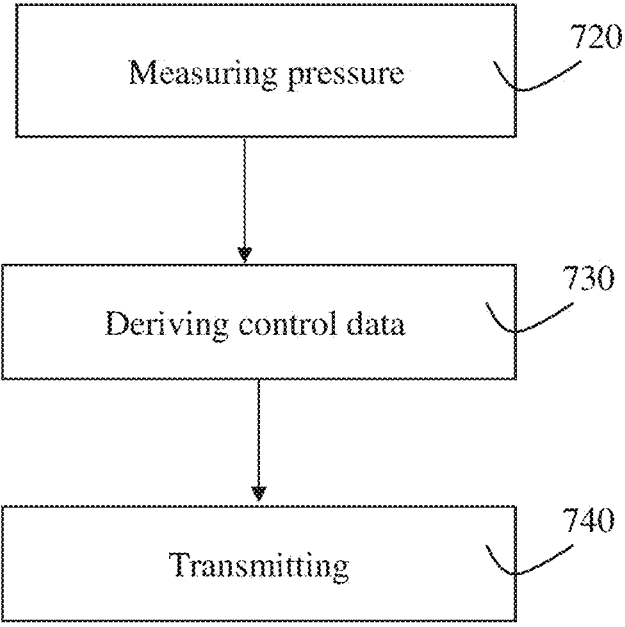
FIG. 7 is a flowchart illustrating a third method for remote controlled physical activity monitoring, according to an exemplary embodiment of the present invention.

Reference is now made to FIG. 7, which is a flowchart illustrating a third method for remote controlled physical activity monitoring, according to an exemplary embodiment of the present invention.

In a third exemplary method, according to an exemplary embodiment of the present invention, during a physical activity—such as swimming, canoe rafting, skiing, etc., a user may remotely control a monitoring of the user's physical activity, even when the user's hands are busy, as described in further detail hereinabove.

In the exemplary method, the user wears an apparatus, say apparatus 4000, on one or more body parts of the user, as described in further detail hereinabove, and as illustrated, for example, in FIG. 1A, 1B.

The apparatus 4000 is used by the user, for remote controlling a physical activity monitoring of the user by a physical activity monitoring device, as described in further detail hereinabove.

In the method, there is measured 720 pressure applied by muscle of one or more body parts of the user, say using the pressure meters 420 of apparatus 4000.

Optionally, the pressure meters 420 include one or more pairs of pressure meters 420 which are arranged on the strap, bracelet, or shirt, such that when the strap, bracelet, or shirt is worn by the user, each two pressure meters 420 of a pair are deployed on preferable areas of the user's body part wearing that pair.

In one example, the pair of pressure meters 420 is positioned over opposite sides of a muscle of the body part wearing the pair of pressure meters 420, say a first pressure meter 420 opposite a second pressure meter 420.

The two pressure meters 420 of each pair may serve as control references for each other, as providers of complementary information (i.e. measurements), etc., as described in further detail hereinbelow.

Next, there is derived 730 monitoring control data from the measured 720 pressure, say by the computer processor 430 of apparatus 4000, as described in further detail hereinabove.

Optionally, there may be compared a measurement 720 of a first one of the pressure meters 420 with a measurement 720 of a second one of the pressure meters 420, for deriving 730 the monitoring control data.

In one example, the computer processor 430 may use measurements 720 of two pressure meters 420 deployed on opposite sides of the muscle of the body part wearing the pressure meters 420, as control references of each other, for deriving 730 the monitoring control data. For example, the computer processor 430 may verify that the two measurements 720 do not significantly differ from each other.

In a second example, the computer processor 430 may use measurements 720 of two pressure meters 420 deployed on opposite sides of the muscle of the body part wearing the pressure meters 420, as complementary information, for deriving 730 the monitoring control data.

For example, the computer processor 430 may use calculations based on measurements 720 by both pressure meters 420 of the pair, for deriving 730 the monitoring control data.

Then, the monitoring control data is transmitted 740 to the physical activity monitoring device, so as to control a monitoring of the user's physical activity, as described in further detail hereinabove.

On the physical activity monitoring device, there are carried out steps of monitoring the user's physical activity, based on the monitoring control data, in real time or near real time.

The steps may include, but are not limited: a step of capturing a stills image of the user with a camera, a step of starting a stopwatch, a step of capturing and recording a vocal comment of the user, a step of moving the physical activity monitoring device into a position closer to the user, etc., as described in further detail hereinabove.

The physical activity monitoring device may include one or more hardware and/or software components, say an aerial vehicle such a quadcopter, a controller which controls the movement of the vehicle—say a programmed microchip which controls the aerial vehicle's rotor engines, wings, etc., as described in further detail hereinabove.

The physical activity monitoring device of the example further may further include other components. The other components may include, but are not limited to: a camera—for capturing stills and/or video images of the user, a microphone—say for allowing the user to vocally comment on events, in real time, during the physical activity, etc., or any combination thereof.

The components of the physical activity monitoring device may alternatively or additionally include a stopwatch, a timer, a data storage, a cellular modem—say for forwarding the images and vocal comments, live to a remote computer, etc., or any combination thereof.

In one example, the physical activity monitoring device includes an aerial vehicle which carries a camera and a controller. Based on the monitoring control data, the controller control the vehicle's engines, so as to maneuver the aerial vehicle, and operates the camera, as described in further detail hereinabove.

Optionally, the method further includes analyzing the user's body movement based on images captured by the camera, say using a software module implemented on the physical activity monitoring device, on a computer in remote communication with the physical activity monitoring device, etc., as described in further detail hereinbelow.

Optionally, the monitoring control data is transmitted 740 to the physical activity monitoring device over a wired connection. For example, the monitoring control data may be transmitted 740 over wires, or rather wirelessly, say as radio-frequency (RF) signals in the Bluetooth® frequency range (2.400 GHz-2.480 GHz).

In a first example, the monitoring control data are derived 730 in a format which is already executable by a component of the physical activity monitoring device, say in a format already executable by the controller of a camera of the physical activity monitoring device, for actuating the camera to zoom in on the user.

In a second example, the monitoring control data are derived 730 in a format which is not yet ready for execution by the component of the physical activity monitoring device, say in a format which is not executable by the controller of the camera of the physical activity monitoring device.

However, in the second example, the method further includes a step of conversion by a computer program which runs on a computer processor of the physical activity monitoring device. Upon receipt of the monitoring control data, the computer program converts the received monitoring control data into a format executable by the camera's controller.

Stated differently, with the exemplary method, the measured 720 changes in the pressure are converted into operational data (say instructions) included in the monitoring control data.

The operational data causes the physical activity monitoring device to carry out operations of monitoring the user, as predefined for the specific measured 720 changes—say to take an image of the user, to start a stopwatch, to maneuver a quadcopter into a position closer to the user, etc.

In one example, there is translated a pressure change measured 720 by one or more of the pressure meters 720, into the operational data included in the monitoring control data, as described in further detail hereinbelow.

Consequently, the user is allowed to control the physical activity monitoring device, even if during the user's physical activity, the user's hands are busy (say busy holding to an axe during ice climbing, or busy rowing during rafting), as described in further detail hereinabove.

It is expected that during the life of this patent many relevant devices and systems will be developed and the scope of the terms herein, particularly of the terms "Computer", "Computer Processor", "Controller", "Electric Circuit", "Wires", "Radio Frequency (RF) Signals", "Gyroscope", "GPS (Global Positioning System)", "Differential GPS", "IMU (Inertial Measurement Unit)", "Conductive Polymer", "Pressure Sensor", "FSR (Force Sensing Resistor)", "Capacitive-based Pressure Sensor", "Electromagnetic Pressure Sensor", "Camera", and "Quadcopter", is intended to include all such new technologies a priori.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. An apparatus for remote controlled physical activity monitoring, the apparatus comprising:
   at least one orientation measurer, wearable on a body part of a user, configured to measure orientation of the body part wearing the at least one orientation measurer during a physical activity of the user;
   a computer processor configured to derive monitoring control data from the measured orientation; and
   a data transmitter configured to transmit the monitoring control data to a physical activity monitoring device to control monitoring of the physical activity of the user by the physical activity monitoring device.

2. The apparatus of claim 1, wherein the at least one orientation measurer further comprises at least two orientation measurers, and wherein the computer processor is further configured to compare a first measurement of a first orientation measurer of the at least two orientation measurers with a second measurement of a second orientation measurer of the at least two orientation measurers for deriving the monitoring control data.

3. The apparatus of claim 1, wherein the at least one orientation measurer comprises at least one of: a Global Positioning System (GPS) receiver, a Differential GPS receiver, or an Inertial Measurement Unit (IMU).

4. The apparatus of claim 1, wherein the computer processor is further configured to translate an angular orientation change measured by the at least one orientation measurer into operation data included in the monitoring control data.

5. The apparatus of claim 1, wherein the computer processor is further configured to translate a movement in a predefined direction measured by the at least one orientation measurer into operation data included in the monitoring control data.

6. The apparatus of claim 1, further comprising the physical activity monitoring device, wherein the physical activity monitoring device comprises a controller and at least one of a camera or a vehicle, and wherein the controller is configured to (i) control an operation of the camera based on the monitoring control data when the physical activity monitoring device comprises the camera and (ii) maneuver the vehicle based on the monitoring control data when the physical activity monitoring device comprises the vehicle.

7. The apparatus of claim 1, further comprising at least one pressure meter, wearable on the body part of the user, configured to measure pressure applied by muscle of the body part wearing the at least one pressure meter during the physical activity of the user, wherein the computer processor is further configured to derive the monitoring control data from the measured orientation and the measured pressure.

8. The apparatus of claim 7, wherein the at least one pressure meter further comprises at least two pressure meters, and wherein the computer processor is further configured to compare a first measurement of a first pressure meter of the at least two pressure meters with a second measurement of a second pressure meter of the at least two pressure meters for deriving the monitoring control data.

9. The apparatus of claim 7, wherein the at least one pressure meter comprises a Force Sensing Resistor (FSR).

10. The apparatus of claim 7, wherein the computer processor is further configured to translate a pressure change measured by the at least one pressure meter into operation data included in the monitoring control data.

11. A method for remote controlled physical activity monitoring, the method comprising:
  measuring, by at least one orientation measurer, an orientation of a body part of a user during a physical activity of the user;
  deriving monitoring control data from the measured orientation; and
  transmitting the monitoring control data to a physical activity monitoring device to control monitoring of the physical activity of the user by the physical activity monitoring device.

12. The method of claim 11, wherein the at least one orientation measurer further comprises at least two orientation measurers, and further comprising:
  comparing a first measurement of a first orientation measurer of the at least two orientation measurers with a second measurement of a second orientation measurer of the at least two orientation measurers for deriving the monitoring control data.

13. The method of claim 11, wherein the at least one orientation measurer comprises at least one of: a Global Positioning System (GPS) receiver, a Differential GPS receiver, or an Inertial Measurement Unit (IMU).

14. The method of claim 11, further comprising translating an angular orientation change measured by the at least one orientation measurer into operation data included in the monitoring control data.

15. The method of claim 11, further comprising translating a movement in a predefined direction measured by the at least one orientation measurer into operation data included in the monitoring control data.

16. The method of claim 11, further comprising at least one of (i) controlling an operation of a camera of the physical activity monitoring device based on the monitoring control data when the physical activity monitoring device comprises the camera and (ii) maneuvering a vehicle of the physical activity monitoring device based on the monitoring control data when the physical activity monitoring device comprises the vehicle.

17. The method of claim 11, further comprising measuring, by at least one pressure meter, pressure applied by muscle of the body part wearing the at least one pressure meter during the physical activity of the user, and wherein deriving the monitoring control data further comprises deriving the monitoring control data from the measured orientation and the measured pressure.

18. The method of claim 17, wherein the at least one pressure meter further comprises at least two pressure meters, and further comprising:
  comparing a first measurement of a first pressure meter of the at least two pressure meters with a second measurement of a second pressure meter of the at least two pressure meters for deriving the monitoring control data.

19. The method of claim 17, wherein the at least one pressure meter comprises a Force Sensing Resistor (FSR).

20. The method of claim 17, further comprising translating a pressure change measured by the at least one pressure meter into operation data included in the monitoring control data.

* * * * *